(12) United States Patent
Amar (10) Patent No.: US 7,626,007 B2
(45) Date of Patent: Dec. 1, 2009

(54) TRANSCRIPTION FACTOR REGULATING TNF-α

(75) Inventor: Salomon Amar, Brookline, MA (US)

(73) Assignee: Trustees of Boston University, Boston, MA (US)

( * ) Notice: Subject to any disclaimer, the term of this patent is extended or adjusted under 35 U.S.C. 154(b) by 258 days.

(21) Appl. No.: 10/405,738

(22) Filed: Apr. 2, 2003

(65) Prior Publication Data

US 2003/0166159 A1 Sep. 4, 2003

Related U.S. Application Data

(62) Division of application No. 09/547,461, filed on Apr. 12, 2000, now Pat. No. 6,566,501.

(60) Provisional application No. 60/128,875, filed on Apr. 12, 1999.

(51) Int. Cl.
 *A01N 43/04* (2006.01)
 *A61K 31/70* (2006.01)
 *C07H 19/00* (2006.01)
 *C07H 21/00* (2006.01)

(52) U.S. Cl. .................... 536/23.1; 536/22.1; 536/24.1; 514/44

(58) Field of Classification Search ................. 435/69.1, 435/320.1, 254.1; 536/23.1, 23.5, 24.5, 24.1; 514/44

See application file for complete search history.

(56) References Cited

U.S. PATENT DOCUMENTS 6,077,693 A 6/2000 Tang et al.

OTHER PUBLICATIONS

Kalota, et al. (2006) Progress in the Development of Nucleic Acid Therapeutics. Hep, v.173: 173-196.*
Takashiba et al., Infect. Immun. 63: 1529-1534 (1995).
Neuenschwander et al., Endocrinology 136: 4298-4303 (1995).
Stein, C.A., Antisense and Nucleic Acid Drug Dev. 8: 129-132 (1998).
Helene et al., Ciba Foundation Symposium 209: 94-102 (1997).
Agrawal and Iyer, Pharm. Ther. 76: 151-160 (1997).
Yao et al., J. of Biol. Chem. 272(28): 17795-801 (1997).
Beutler er al., Science 229: 869-871 (1985).
Tracey et al., Science 234: 470-474 (1986).
Miethke et al., J. Exp. Med. 175:91-98 (1992).
Tracey et al., J. Exp. Med. 167: 1211-1227 (1988).
Rink and Kirchner, Int. Arch. Allergy Immunol. 111: 199-209 (1996).
Polyak et al., Nature Sep. 18; 389 (6648): 300-305 (1997).
Amar and Myokai, GenBank deposit U77396 (1996).
Amar and Myokai, GenBank deposit NM 004862 (1996).

* cited by examiner

*Primary Examiner*—Sean R McGarry
*Assistant Examiner*—Jennifer Pitrak
(74) *Attorney, Agent, or Firm*—Clark & Elbing LLP (57) ABSTRACT

Disclosed herein is an isolated polypeptide comprising the amino acid sequence set forth in SEQ ID NO: 1. The isolated polypeptide binds to the DNA binding domain located from −550 to −487 in the promoter of the human TNF-α gene. Additionally, the level of the mRNA transcript encoding the isolated polypeptide is substantially increased in response to LPS stimulation in cultured THP-1 cells.

9 Claims, 2 Drawing Sheets

```
GTTTCTCTCCCTGCCCCCGCGACTTCGCGCAAGATCCGGGAAGGACACCCGAGGCCCCTG    60
GGAGACCCTGGGGAGGTGAAAGTCAGAGAGCGAAGCGGGCCGTGGCCCCTAGGCCTGACC   120
CCTCCCCGCGGGGTAAGGCGGGCACCCCGCGAGCGCAGGGGTCCTCTTACTGCTGATGGC   180
ACCCAGCTCTGGGCCCAGACGCCGCTCACCGTCCACCGCCGGTGCTGGGTAAAATGTCGG   240
                                                    M  S  V    3
TTCCAGGACCTTACCAGGCGGCCACTGGGCCTTCCTCAGCACCATCCGCACCTCCATCCT   300
 P  G  P  Y  Q  A  A  T  G  P  S  S  A  P  S  A  P  P  S  Y   23
ATGAAGAGACAGTGGCTGTTAACAGTTATTACCCCACACCTCCAGCTCCCATGCCTGGGC   360
 E  E  T  V  A  V  N  S  Y  Y  P  T  P  P  A  P  M  P  G  P   43
CAACTACGGGCTTGTGACGGGGCCTGATGGGAAGGGCATGAATCCTCCTTCGTATTATA   420
 T  T  G  L  V  T  G  P  D  G  K  G  M  N  P  P  S  Y  Y  T   63
CCCAGCCAGCGCCCATCCCCAATAACAATCCAATTACCGTGCAGACGGTCTACGTGCAGC   480
 Q  P  A  P  I  P  N  N  N  P  I  T  V  Q  T  V  Y  V  Q  H   83
ACCCCATCACCTTTTTGGACCGCCCTATCCAAATGTGTTGTCCTTCCTGCAACAAGATGA   540
 P  I  T  F  L  D  R  P  I  Q  M  C  C  P  S  C  N  K  M  I  103
TCGTGAGTCAGCTGTCCTATAACGCCGGTGCTCTGACCTGGCTGTCCTGCGGGAGCCTGT   600
 V  S  Q  L  S  Y  N  A  G  A  L  T  W  L  S  C  G  S  L  C  123
GCCTGCTGGGGGTGCATAGCGGGCTGCTGCTTCATCCCCTTCTGCGTGGATGCCCTGCAG   660
 L  L  G  V  H  S  G  L  L  L  H  P  L  L  R  G  C  P  A  G  143
GACGTGGACCATTACTGTCCCAACTGCAGAGCTCTCCTGGGCACCTACAAGCGTTTGTAG   720
 R  G  P  L  L  S  Q  L  Q  S  S  P  G  H  L  Q  A  F  V  G  163
GACTCAGCCAGACGTGGAGGGAGCCGGGTGCCGCAGGAAGTCCTTTCCACCTCTCATCCA   780
 L  S  Q  T  W  R  E  P  G  A  A  G  S  P  F  H  L  S  S  183
GCTTCACGCCTGGTGGAGGTTCTGCCCTGGTGGTCTCACCTCTCCAGGGGGCCCACCTTC   840
 F  T  P  G  G  S  A  L  V  V  S  P  L  Q  G  A  H  L  H  203
ATGTCTTCTTTTTGGGGGGAATACGTCGCAAAACTAACAAATCTCCAAACCCCAGAAATTG   900
 V  F  F  W  G  E  Y  V  A  K  L  T  N  L  Q  T  P  E  I  A  223
CTGCTTGGAGTCGTGCATAGGACTTGCAAAGACATTCCCCTTGAGTGTCAGTTCCACGGT   960
 A  W  S  R  A  *                                             228
TTCCTGCCTCCCTGAGACCCTGAGTCCTGCCATCTAACTGTGATCATTGCCCTATCCGAA  1020
TATCTTCCTGTGATCTGCCATCAGTGGCTCTTTTTTTCCTGCTTCCATGGGCCTTTCTGGT  1080
GGCAGTCTCAAACTGAGAAGCCACAGTTGCCTTATTTTTTGAGGCTGTTCTGCCCAGAGCT  1140
CGGCTGAACCAGCCTTTAGTGCCTACCATTATCTTATCCGTCTCTTCCCGTCCCTGATGA  1200
CAAAGATCTTGCCTTACAGACTTTACAGGCTTGGCTTTGAGATTCTGTAACTGCAGACTT  1260
CATTAGCACACAGATTCACTTTAATTTCTTAATTTTTTTTTTAAATACAAGGAGGGGGCT  1320
ATTAACACCCAGTACAGACATATCCACAAGGTCGTAAATGCATGCTAGAAAAATAGGGCT  1380
GGATCTTATCACTGCCCTGTCTCCCCTTGTTTCTCTGTGCCAGATCTTCAGTGCCCCTTT  1440
CCATACAGGGATTTTTTTCTCATAGAGTAATTATATGAACAGTTTTTATGACCTCCTTTT  1500
GGTCTGAAATACTTTTGAACAGAATTTCTTTTTTTTAAAAAAAAACAGAGATGGGGTC TT  1560
ACTATGTTGCCCAGGCTGGTGTCGAACTCCTGGGCTCAAGCGATCCTTCTGCCTTGGCCT  1620
CCCGAAGTGCTGGGATTGCAGGCATAAGCTACCATGCTGGGCCTGAACATAATTTCAAGA  1680
GGAGGATTTATAAAACCATTTCTGTAATCAAATGATTGGTGTCATTTTCCCATTTGCCA  1740
ATGTAGTCTCACTTAAAAAAAAAAAAAAAAAAAAA                           1773
```

*FIG. 2*

TRANSCRIPTION FACTOR REGULATING TNF-α

RELATED APPLICATIONS

This application is a divisional of U.S. application Ser. No. 09/547,461, filed on Apr. 12, 2000, now U.S. Pat. No. 6,566,501, which claims priority from U.S. Provisional Application No. 60/128,875, filed Apr. 12, 1999.

GOVERNMENT SUPPORT

This invention was made with Government Support under Contract Number DE-10709 awarded by the National Institute of Craniofacial and Dental Research. The Government has certain rights in the invention.

BACKGROUND OF THE INVENTION

The innate host response to bacterial pathogens is characterized by an immediate release of biologically active compounds, including monokines and cytokines. These proinflammatory molecules, which are intended to enable the host to eliminate the pathogen, may also adversely affect the host. In acute situations, the pathogen is often eliminated, with resolution of inflammation and minimal tissue damage. However, failure to control the pathogen often leads to a state of metabolic anarchy in which the inflammatory response is not controlled and significant tissue damage results. Endotoxins, produced from the outer membrane of Gram-negative bacteria, and exotoxins, released from the cell wall of Gram-positive bacteria, are known to be potent inducers of the inflammatory response. Lipopolysaccharide (LPS), extracted from the outer membrane of Gram-negative bacteria, has been identified as a principal endotoxic component.

Although the inflammatory response is mediated by a variety of secreted factors, the cytotoxic effects of LPS have been ascribed to TNF-α activity (Beutler et al., *Science* 229: 869-871 (1985); Tracey et al., *Science* 234: 470-474 (1986); Miethke et al., *J. Exp. Med.* 175: 91-98 (1992)). TNF-α is a pleiotropic cytokine which serves to either benefit the host or in some situations exert detrimental effects on the host (Beutler and Cerami, *Nature* 320: 584-588 (1986); Beutler et al., *Science* 232: 977-980 (1986); Beutler and Cerami, *N. Engl. J. Med.* 316: 379-385 (1987)). TNF-α benefits the host by helping to prevent cancer, protecting against infection, promoting tissue remodeling, and activating inflammatory responses. Conversely, in host responses which have gone awry, TNF-α mediates septic shock in chronic infections, is responsible for cachexia in cancer patients, causes inflammation in rheumatoid arthritis patients, and activates the human immunodeficiency virus. The pleiotropic effects of TNF-α are dose-dependent. Hence, the perceived need to control TNF-α production has raised interest into the understanding of the mechanisms that modulate TNF-α gene expression.

It is well known that gene transcription is controlled by DNA-binding proteins. Recently, several groups have examined the transcriptional regulation of TNF-α by various inducers, such as virus, LPS, and PMA. The human TNF-α promoter contains motifs that resemble nuclear factor kappa B (NF-κB) binding sites; however, controversy exists as to the involvement of NF-κB in TNF-α gene regulation. The nature of the nuclear factor(s) involved in the regulation of LPS-induced TNF-α gene expression in humans remains unknown.

SUMMARY OF THE INVENTION

In one aspect, the present invention relates to an isolated polypeptide which binds to the DNA binding domain located from −550 to −487 in the promoter of the human TNF-α gene. This isolated polypeptide is referred to herein as the LITAF protein. In one embodiment, the isolated polypeptide is mammalian in origin. In a preferred embodiment, it is human or murine.

In another aspect the present invention relates to a nucleic acid sequences which encodes the LITAF protein. Nucleic acid sequences which are characterized by the ability to hybridize to the complement of the nucleic acid sequence of the present invention under stringent hybridization conditions are also encompassed by the present invention. Also encompassed is an expression vector comprising a nucleic acid sequence which encodes the LITAF protein. Also encompassed is a cell containing said expression vector, and a mammalian gene which encodes the LITAF protein. Preferably, the gene is human and is located on Chromosome 16 p12-16p13.3.

In another aspect, the present invention relates to an antibody characterized by the ability to specifically bind to the LITAF protein. The antibody may be monoclonal or polyclonal.

Another aspect of the present invention relates to a method for inhibiting LITAF dependent induction of TNF-α gene expression in a cell, comprising the steps a) providing an inhibitor of expression of the LITAF gene; and b) delivering the inhibitor into the cell. In one embodiment, the inhibitor is an antisense construct which encodes an antisense RNA molecule which is complementary to a portion of the LITAF mRNA which is greater than 200 nucleotides in length. Preferably, the antisense RNA molecule is complementary to the start site of translation, upstream adjacent 5' untranslated sequence, and downstream adjacent coding sequence of the LITAF mRNA. Optimal lengths and specific nucleotides for complementary are discussed.

Another aspect of the present invention relates to a method for inhibiting LITAF dependent induction of TNF-α gene expression in a cell comprising the steps a) providing an inhibitor of LITAF protein function; and b) contacting the inhibitor to the LITAF in the cell. In one embodiment, the inhibitor is an antibody which binds the LITAF protein. In another embodiment the inhibitor is a small molecule which inhibits the function of the LITAF protein. One example of such an inhibitor is a recombinant mutant LITAF protein.

Therapeutic methods for treating a patient with a disease associated with chronic inflammation, by administration of the LITAF inhibitor to the patient are also provided. Such diseases include rheumatoid arthritis, gum disease Crohn's disease, and graft-versus-host disease. Therapeutic methods for treating a patient with a disease in which TNF-α plays a role in pathology are also provided. Examples of such diseases are diabetes mellitus, cancer, cachexia, breast cancer, HIV, sepsis, malaria, trypanomiasis and asthma. Other methods provided include a method for identifying gene which are regulated by the LITAF protein, a method for identifying a molecule which inhibits LITAF binding to the TNF-α promoter, and a method for identifying molecules which bind LITAF from a protein array.

BRIEF DESCRIPTION OF THE FIGURES

FIG. 1A is an illustration of the physical map of the LITAF cDNA isolated. The thicker line denotes the open reading frame (from AUG 234 to UAG 918) in LITAF. Restriction sites for EcoRI, HincII, PstI, SacI and ApaI are shown. Note that the antisense RNA represented as AS5' was designed to be complementary to the 5' region of LITAF mRNA between the restriction sites (EcoRI and HincII). However, the full length LITAF was used as sense RNA for overexpression of LITAF RNA and is shown below AS5' as SE.

FIG. 2 is the nucleotide sequence of LITAF SEQ ID NO: 2 and its deduced amino acid sequence SEQ ID NO: 1 (Genbank accession number U77396). The full length of LITAF cDNA was isolated from a cDNA library of PMA-differentiated THP-1 cells stimulated with LPS. The open reading frame encodes 228 amino-acids with a predicted molecular weight of 23.9 kD. The Alu sequence is underlined.

DETAILED DESCRIPTION OF THE INVENTION

The present invention is based on the identification of a protein which binds the promoter of the TNF-α gene and activates gene transcription. In one respect, the present invention relates to the isolated polypeptide which is characterized by the ability to bind to the DNA sequence domain located from −550 to −487 in the human TNF-α promoter (Takashiba et al., *Infect. Immun.* 63: 1529-1534 (1995)). The polypeptide isolated from human cells is a 23.9 kD protein, and has been named LITAF. Human LITAF has 228 amino acids, listed in FIG. 2, and is also designated as SEQ ID NO: 1. Despite being identified via binding to a DNA-binding domain, a search of the public nucleotide and protein sequence databases indicates that LITAF contains no sequences similar to presently known DNA-binding motifs.

Equivalents of LITAF are also encompassed by the present invention. The term equivalent, as used herein, is meant to include LITAF homologs from different organisms (e.g., other mammals, avians, yeasts, *C. elegans*, and *Drosophila*). Such homologs can be identified by one of skill in the art through routine experimentation. Also included in the term equivalent are polypeptides which result from amino acid sequence variations of the LITAF polypeptide listed in SEQ ID NO: 1, which do not significantly affect function. Such sequence variations can be substitutional, insertional or deletional. Substitutional sequence variation equivalents typically contain the exchange of one amino acid for another at one or more sites within the polypeptide, and may be designed to modulate one or more properties of the polypeptide, such as stability against proteolytic cleavage, without the loss of other functions or properties. Substitutions of this kind preferably are conservative, that is one amino acid is replaced with one of similar shape and charge. Conservative substitutions are well known in the art. Deletional sequence variation equivalents lack one or more residues of the native protein which are not essential for function or immunogenic activity. Insertional sequence variation equivalents typically involve the addition of material at a non-terminal point in the polypeptide. This may include insertion of an immunoreactive epitope or simply a single residue. Terminal additions, otherwise called fusions, are made to the protein without loss of protein function, and often result in an addition of another function (e.g., the ability to bind another protein, or the ability to be detected in a standardized detection assay).

The above described LITAF polypeptide, and equivalents are useful as antigenic polypeptides in the generation and/or isolation of antibodies which specifically bind LITAF. In addition to using the full length LITAF polypeptide, fragments of the polypeptide are also useful in generating antibodies which specifically recognize the full length polypeptide or a fragment thereof. In one embodiment, the present invention is an antigenic fusion protein comprised of full length LITAF or a fragment thereof, used to generate antibodies which bind the respective region of the LITAF protein.

Another aspect of the present invention relates to antibodies which are characterized by the ability to specifically bind the LITAF protein and/or the equivalents thereof. Antibodies of the present invention can be monoclonal or polyclonal. The antibodies are either specifically generated by immunization of an animal with the antigenic protein or fragment, or alternatively are identified from preexisting antibodies (e.g., a combinatorial library) via binding affinity.

Another aspect of the present invention involves nucleic acid sequences which encode the LITAF protein, or encode an equivalent of LITAF. The nucleotide sequence of a cDNA made from a mRNA which encodes human LITAF is listed in FIG. 2, and is also designated as SEQ ID NO: 2. The cDNA contains an ORF, and 5' and 3' untranslated sequences. Sequences derived from this cDNA are useful in the identification and purification of cDNAs for LITAF homologs, and also in the identification of LITAF genes. Nucleic acid sequences which hybridize to the complement of the nucleic acid sequence of SEQ ID NO: 2 under stringent hybridization conditions can be identified by one of average skill in the art through routine experimentation, and as such are encompassed by the present invention.

The nucleic acid sequences of the present invention or fragments thereof can be inserted into a vector used to propagate the sequences in a cell. Such vectors are introduced into cells (e.g., prokaryotic or eukaryotic), and the cells are propagated to produce multiple copies of the vector. A useful type of vector is an expression vector. Coding regions of the nucleic acid sequences of the present invention or fragments thereof can be inserted into an expression vector under conditions appropriate for expression of the sequences. Such vectors, are introduced into cells (e.g., prokaryotic or eukaryotic cells) under conditions appropriate for expression. The expressed protein is purified from the cells by routine methods. In one embodiment, the cell is eukaryotic (e.g., mammalian, avian, insect, or yeast). In a preferred embodiment, the cell is human.

Another aspect of the present invention is the gene which encodes the LITAF polypeptide. As detailed in the Exemplification section below, the LITAF gene is found at a locus on Chromosome 16 p12-16p13.3. Genes which encode LITAF homologs can be identified in other species of mammals and in more distantly related organisms using the sequence information herein. For instance, identification of a yeast homolog for LITAF would be extremely useful in studying the involvement of LITAF in signal transduction.

The present invention also provides a method for blocking LITAF induced transcription of the TNF-α gene in a cell. The finding that the LITAF protein is involved in lipopolysaccharide induced TNF-α gene expression, indicates that one way in which signals in the cell induce gene transcription of TNF-α is through activation of the promoter binding and gene inducing activity of LITAF. Such activation of TNF-α gene expression is referred to herein as LITAF dependent. Experiments detailed in the Exemplification section below indicate that lipopolysaccharide induction of TNF-α gene expression is LITAF dependent. In addition, the present invention can also be used to block other processes and signals in a cell which induce TNF-α gene expression via a LITAF dependent mechanism.

Several types of inhibitors can be devised and used to inhibit LITAF dependent induction of TNF-α gene expression. Inhibitors include, without limitation, inhibitors of LITAF expression, and inhibitors of LITAF function. Experiments detailed in the Exemplification indicate that one way of inhibiting LITAF gene expression is via antisense technology. Antisense inhibition of LITAF can be accomplished using an antisense construct which encodes an RNA (an antisense RNA) which is complementary to a portion of the LITAF mRNA. Preferably the antisense RNA is between 200 nucleotides and the entire length of the LITAF mRNA. In a preferred embodiment, the antisense RNA is about 320 bases. The antisense RNA can be complementary to any isolated region of the LITAF mRNA. In one embodiment, the antisense RNA is complementary to the 5' region of the LITAF mRNA. In a related embodiment, the antisense RNA includes a region that is complementary to the translation start site. In a preferred embodiment, the complementary region encompasses the start site of translation and also encompasses upstream adjacent 5' untranslated sequence and downstream adjacent coding sequence. One specific antisense RNA which has been demonstrated to function in the inhibition of LITAF expression has a sequence corresponding to nucleotides 1-320 of SEQ ID NO: 2. Other antisense RNAs which are the same length, and overlap the sequence of nucleotides 1-320 of SEQ ID NO: 2, including at least 10-20 bases of the 5' untranslated region, have also been determined by applicants to be equally affective at inhibition of LITAF expression.

Antisense technology can also be accomplished using synthesized oligonucleotides, or functional equivalents thereof, as an inhibitor to disrupt LITAF gene expression. The oligonucleotide is either complementary to the LITAF gene or the LITAF mRNA and delivery of multiple copies of the oligonucleotide into a target cells inhibits LITAF gene expression of LITAF in the cell at either the level of transcription or translation, respectively. In one embodiment, the oligonucleotide is complementary to a contiguous portion of the LITAF mRNA which is greater than 150 nucleotides. Both oligonucleotides and antisense RNA used in the above method must be delivered into the cell in which inhibition of TNF-α is desired. Many methods of delivery of nucleic acids into cells are well know in the art. Some examples include, without limitation, electroporation, microinjection, calcium phosphate transfection, cellular import signal peptide mediated delivery, receptor mediated uptake, and liposome mediated delivery. The particular method of delivery of the nucleic acid into the cell depends upon the circumstances of the individual cell (e.g., the cell type, the environment of the cell, the amount of inhibitor to be delivered), and must be determined on a case by case basis by the skilled practitioner.

LITAF dependent TNF-α gene induction can also be inhibited through utilization of an inhibitor of LITAF protein function. One way to inhibit LITAF function is to inhibit LITAF DNA binding. The LITAF protein binds to the promoter of TNF-α to induce gene transcription. An inhibitor which interferes with LITAF binding to the promoter region will prevent LITAF dependent gene induction. Inhibitors can interfere with binding through competitive inhibition or by disabling the LITAF protein. One example of an inhibitor is a mutant LITAF protein which retains the ability to bind the promoter region, but cannot induce gene transcription. Such a mutant would competitively inhibit the ability of native LITAF to bind the promoter. The generation of such a mutant is described in detail below. Another example of an inhibitor is a molecule which binds native LITAF (e.g., a small molecule or an antibody) and prevents it from binding the promoter. Another example is a molecule which binds LITAF (e.g., a small molecule or an antibody) and inhibits LITAF binding to another molecule (e.g., a regulatory molecule), the binding of which is necessary for LITAF activity. Another example of an inhibitor of the LITAF protein is a molecule which catalyzes the degradation of the LITAF molecule, such as an antibody which catalyzes the hydrolysis of LITAF.

TNF-α has been shown to be involved in the pathologies of several diseases. Several of these diseases are characterized by chronic inflammation. These diseases include, without limitation, rheumatoid arthritis, gum disease, Crohn's disease, and graft-versus-host disease. In infectious diseases, failure to control the pathogen often leads to an uncontrolled inflammatory response which causes significant tissue damage, as with septic shock in chronic and acute infections. The involvement in pathologies of TNF-α is not limited to causing inflammation, as evidenced by its involvement in other diseases where the direct effect of TNF-α is less clear. Without limitation, TNF-α is known to contribute to pathologies in diabetes mellitus, cancer, HIV, sepsis, asthma, malaria, and trypanomiasis (Rink et al., *Int. Arch Allergy Immunol* 111: 199-209 (1996)). The involvement of TNF-α in cancer includes the pathology of cachexia in cancer patients, and also the development and/or progression of breast cancer. The present invention finds use therapeutically in inhibiting TNF-α gene expression in patients with such diseases. Because the pleiotropic effects of TNF-α are dose-dependent (Tracey et al., *J. Exp. Med.* 167: 1221-1227 (1988)), administration of one or more of the above described inhibitors of LITAF (inclusive of both inhibitors of LITAF transcription and inhibitors of LITAF protein function) to a patient suffering from one of these diseases, to effect an inhibition of TNF-α gene induction, will produce a therapeutic effect.

Because LITAF is an intracellular protein, administration of the LITAF inhibitor must deliver the inhibitor into the cells of the patient to affect LITAF function. Exactly which cells are to be targeted for delivery depends upon the particular disease from which the patient suffers, and can be determined by one of skill in the art. For example, when treating a patient with cancer the inhibitor may be delivered to the cancer cells of the patient. Appropriate administration to affect delivery into the cells may be facilitated by formulating the inhibitor with a carrier which promotes cellular uptake (e.g., within a liposome) or the inhibitor itself may be modified for cellular targeting (e.g., attached to a cellular uptake signal sequence, or encoded within a viral vector). A variety of modes of delivery of molecules into cells are known and available to one of skill in the art. Such methods include, without limitation, virus mediated gene transfer, especially adenovirus mediated gene transfer, liposome mediated delivery of nucleic acids and polypeptides into cells, antibody mediated delivery of molecules into cells. A variety of techniques delivery of oligonucleotides and their equivalents into a cell are described by L. M. Neckers (Gene Therapeutics Methods and Applications of Direct Gene Transfer, P. 180-192, Jon A. Wolff, Editor, Birkhauser, Boston, Mass.). These methods include, without limitation, internalization of unmodified oligonucleotide, internalization of oligonucleotides that are 1) methylphosphonates, 2) phosphorothiolates, 3) modified with pendent groups such as poly L-lysine, avidin, cholesterol or phospholypid moieties, C5 oligonucleotide containing propynyl pyrimidine, or are liposome encapsulated). Also included in the present invention is the method of delivery of oligonucleotides into a cell via the method of Brand et al. (*Journal of Investigative Dermatology* 111: 1166-71 (1998)). Methods for specifically targeting a molecule to a subset of cells are also known in the art, and include without limitation, antibody mediated delivery, and direct application or injection into the desired region. The amount of LITAF inhibitor to be administered is the amount necessary to promote delivery of an amount of LITAF inhibitor into the appropriate cells sufficient to suppress LITAF dependent expression of TNF-α in the cells. The exact amount will depend upon a variety of factors, including without limitation, the particular LITAF inhibitor used, the method of administration, and characteristics of the patient (e.g., overall health, weight, metabolism, etc.). This amount is to be determined on a case by case basis by a skilled practitioner.

Another aspect of the present invention relates to the identification of genes which are regulated by LITAF. Evidence presented in the Exemplification section below indicates that LITAF is a DNA binding protein which functions in the regulation of gene transcription. LITAF binding to the human TNF-α promoter sequence from −550 to −487 increases the transcription of the TNF-α gene. Commonly, DNA binding proteins, such as transcription factors, affect the regulation of a plurality of genes, usually by binding to a conserved sequence motif which is common to the promoter region of the regulated genes. The regulation produced by binding can be either positive or negative. The actual regulatory effect the DNA binding protein has on a gene often varies with the particular gene, and is often dependent upon a variety of circumstances, (e.g., interaction with other regulatory proteins). The identification of the LITAF protein enables the identification of additional genes which are regulated by LITAF. One way of accomplishing this is by providing a cell of interest, and treating the cell to increase the amount of active LITAF the cell. Once the active LITAF in the cell is increased, gene expression is allowed to proceed. The gene expression in the treated cell is then compared to the gene expression in an untreated control cell. Genes which are regulated by the activity of LITAF, either induced or suppressed, are identified by comparison to the expression of that gene in the control cell. Genes which are induced by LITAF will have a higher level of expression in the treated cell than the control cell. Conversely, genes which are suppressed by LITAF will have a lower level of expression in the control cell.

The cell used in the method directly above may be of mammalian origin, (e.g., human, murine) or alternatively may be derived from an another organism in which LITAF, or a homolog thereof functions (e.g., avian, *Drosophila*, yeast). In multicellular organisms, the effect of LITAF on gene expression may vary between cell types in an organism. Therefore, examination of a variety of cell types will further the identification of LITAF regulated genes. Cells used in the assay are either primary cells isolated directly from nature (e.g., an organism) or are cells propagated in culture.

It is possible to increase the amount of active LITAF in the cell by a variety of methods known in the art. Some examples include, without limitation, introducing (e.g., via transfection or electroporation) into the cell an expression vector which encodes LITAF, directly introducing the LITAF protein into the cell (e.g., via microinjection or liposome mediated transfer), and increasing the expression or activity of a positive regulator of LITAF molecule. Alternately, an activated mutant of LITAF, discussed in more detail below, can be introduced into the cell (e.g., via introduction of an expression vector which encodes the mutant or direct introduction of the mutant protein into the cell).

Gene expression is allowed to proceed in the cells for a predetermined time period. Genes which are directly regulated by LITAF binding are expected to be either activated or suppressed shortly after the increase in LITAF activity. Several methods are currently available to the skilled practitioner for specific identification of differentially expressed genes of a treated cell versus a control cell (e.g., gene trap and subtractive hybridization). Another method of identifying genes which are regulated by LITAF involves identification of a consensus LITAF binding site and performance of a database search for known promoter regions which contain this sequence. Standard functional analysis is then used to confirm the proposed regulatory participation of LITAF.

Perhaps a more direct method of identifying crucial functions of LITAF is to create an organism which lacks a functional LITAF gene (a knockout organism). Homozygous knockouts are commonly made in mice, and lower organisms. The organisms are then compared to control organisms and deficiencies or other differences are identified. Differences in the knockout are then correlated to any cellular deficiencies that can be identified, which are then traced back to the absence of the missing gene. Another aspect of the present invention relates to the identification of molecules which regulate the LITAF protein. Regulators of the LITAF protein are molecules which directly or indirectly interact with the LITAF protein to promote or inhibit LITAF dependent gene expression. Such regulators are identified by screening candidate molecule (e.g., from a small molecule library or in a combinatorial screening system) using a functional assay system. Such an assay system can be created by linking a functional promoter region containing a functional LITAF DNA binding region (e.g., corresponding to bases −550 and −487 of the human TNF-α promoter region) linked to a reporter molecule. The candidate inhibitor is contacted to the LITAF molecule and then assayed for a regulatory effect. In the assay system, activation or suppression of LITAF dependent transcription indicates activating or inhibitory activity of the candidate molecule, respectively.

Commonly, DNA binding molecules are regulated by mechanisms which enhance or inhibit their DNA binding activity. In this respect, the present invention relates to a method for identifying a molecule which inhibits or enhances LITAF binding to the TNF-α promoter. Such inhibitors or activators can be identified from candidate molecules using a binding assay. The candidate molecule is contacted to LITAF in the assay, and the binding of LITAF to the TNF-α promoter, (or consensus DNA binding sequence) is determined and compared to LITAF binding in the absence of the candidate molecule. Significantly lower binding of LITAF to the promoter region in the presence of the candidate molecule indicates the presence of an inhibitor, significantly higher binding in the presence of the candidate molecule, indicates the presence of an activator.

Another aspect of the present invention relates to the identification and production of recombinant LITAF molecules which have altered function. Recombinant LITAF mutants can be produced in vivo or in vitro and then assayed for function. Mutations in the LITAF molecule are made and the mutant LITAF proteins are then individually tested, or alternatively, selected from a group of mutants for a desired activity, (e.g., binding to the TNF-α promoter region or transcription activation). Mutations are generally amino acid substitution mutations, deletions, or insertions. Mutants which are produced can be used to map functional regions of the LITAF protein. The mutants may also have other uses, for example, mutants which are produced that retain the ability to bind the promoter region, but lack transcription activating activity may prove valuable as dominant negative mutants, acting as competitive inhibitors of LITAF activity when delivered or expressed in cells. Conversely, mutants which have increased activity may be used to study LITAF gene regulation and signal transduction. Mutations in the LITAF molecule are either site directed or randomly made. Regions of interest for site directed mutagenesis can be identified, for example by functional studies (e.g., identifying at what site LITAF binds DNA) or from protein sequence analysis.

Another aspect of the present invention relates to identifying molecules which bind LITAF by screening combinatorial polypeptide libraries which encode either a random or controlled collection of amino acids. One such method is identifying molecules which bind LITAF from a polypeptide array. An array of polypeptides is synthesized on a solid support (e.g., a biological chip) as described by Pirrung et al., U.S. Pat. No. 5,143,854 (1992), the contents of which are incorporated herein by reference. The polypeptides which are attached to the support are called the probe. The resulting product is then processed to determine which polypeptides of the array bind a target protein, in this case LITAF. The array linked support is contacted with the target molecule under conditions appropriate for binding, and specific probe proteins which bind the target molecule are identified. Methods for detecting labeled markers on a support are provided by Trulson et al., U.S. Pat. No. 5,578,832 (1996), the contents of which are incorporated herein by reference.

Another method for identifying polypeptides from a library which bind to a specified molecule is provided by Dower et al., U.S. Pat. No. 5,432,018 (1995), the contents of which are incorporated herein by reference. In addition, libraries of non-polypeptide chemical compounds can be screened for binding to and/or inhibition of LITAF by the method of Zambias et al., U.S. Pat. No. 5,807,754 (1998), the contents of which are incorporated herein by reference, and also the method of J. Ellman, U.S. Pat. No. 5,288,514 (1994) the contents of which are incorporated herein by reference.

Small molecules which bind LITAF identified by the above methods have potential use as inhibitors of LITAF. Such inhibitors may inhibit LITAF binding of DNA or alternatively of regulatory proteins.

EXEMPLIFICATION

Previous studies pertaining to macrophage response to LPS have identified a DNA sequence domain located from −550 to −487 in the human TNF-α promoter (Takashiba et al., *Infect. Immun.* 63: 1529-1534 (1995)). Using electrophoretic shift assays and selective mutations, it was shown that a 64-base pair (bp) fragment located within this region can bind unknown protein(s) and this binding is responsible for TNF-α transcriptional activity. Sequence analysis of this fragment revealed the absence of any potential NF-κB binding sites (Takashiba et al., *Infect. Immun.* 63: 1529-1534 (1995)), suggesting the existence of a cis-acting regulatory protein, other than NF-κB, necessary for human TNF-α gene transcription. The following experiments were performed to isolate and characterize the cis-acting regulatory protein which binds this 64-base pair fragment, now given the name LPS-Induced TNF-Alpha Factor (LITAF).

Cloning the LITAF cDNA

In an effort to elucidate the molecular mechanisms of LPS-induced TNF-α gene regulation, the 64-bp DNA fragment responsible for TNF-α transcriptional activity was used to isolate the native protein which binds to the TNF-α promoter element. Nuclear extracts were prepared from the human monocytic cell line, THP-1. A DNA sequence corresponding to the isolated 64-bp fragment, with a 5' biotin tag was generated and coupled to streptavidin linked inert beads to produce what is referred to herein as affinity beads. The affinity beads were then used to affinity purify the DNA-binding protein from the THP-1 nuclear extracts. The DNA-binding protein obtained was eluted from the beads and subjected to amino acid sequence analysis. Degenerate oligonucleotides which correspond to either end of the deduced peptide fragment M-S-V-P-G-P-Y-Q-A-A-T-G (SEQ ID NO: 3) were used in the polymerase chain reaction (PCR), with LPS-induced THP-1 cDNA. This produced a DNA fragment containing the exact nucleotide sequences encoding the middle part of the isolated peptide. This probe was used to screen a LPS-stimulated, PMA-induced THP-1 cDNA library. The screen identified nine positive clones. The longest cDNA insert obtained (1.8 kb) was then sequenced.

Screening, Sequencing and Structural Analysis of LITAF cDNA

As shown in FIG. 2, the cDNA consists of a 234-nucleotide 5' noncoding region, a 687-nucleotide open reading frame, and an 852-nucleotide 3' noncoding region that includes a poly-A signal. The open reading frame encodes a 228 amino acid 23.9-kD protein (GeneBank accession number U77396). At the time that the DNA sequencing was nearly complete, the coding sequence was determined to have no significant homology with nucleotide and protein sequences available in all public databases. None of the sequences in the coding region were found similar to typical DNA-binding motifs. Isolated sequences in the 5' UTR and 3' UTR displayed some homology with sequences reported in the databases: several amino acid sequences were found similar to the Bicaudal-C gene of *Drosophila melanogaster*. Although the Bicaudal-C gene product contains a motif called the KH domain, which is found in many RNA and single-stranded DNA-binding proteins (Mahone et al., *EMBO J.* 14: 2043-2055 (1995)), a typical KH domain was not found in the LITAF gene.

In addition, sequencing of the LITAF gene revealed Alu elements in the 3' noncoding region (FIG. 2). Several investigators have reported that Alu elements constitute approximately 5% of the human genome and are often found in introns or 3' untranslated regions. However, the Alu region may be mistakenly incorporated into open reading frames (Claverie and Makalowski, *Nature* 371: 752 (1994)). To determine whether the presence of the Alu element was a result of alternative splicing from an adjacent intron, the other two cognate clones were sequenced. The nucleotide sequences of the cognate clones significantly overlapped, indicating that the presence of the Alu region in the cDNA was probably not caused by a splicing error.

The identified DNA sequence was entered in the GeneBank database as a TNF-α-induced mRNA. Following this entry, Polyak et al. (*Nature*, September 18;389(6648): 300-305 (1997)) identified several transcripts markedly induced by p53. Among them an EST named PIG7 was found to harbor 98% homology with TNF-α-induced mRNA (Polyak et al., *Nature*, September 18;389(6648): 300-305 (1997)). This cDNA has since been named LITAF (LPS-Induced TNF-Alpha Factor) because it is induced by LPS and affects TNF-α gene expression.

LITAF mRNA is Induced by LPS mRNA was obtained from THP-1 cells cultured under various conditions: stimulation with P.g. LPS; differentiation with PMA; differentiation with PMA followed by stimulation with LPS; and no stimulation. Northern blot analysis was performed on the RNA produced under each condition, using an antisense RNA probe that corresponded to the LITAF cDNA coding region. A single band which migrated at 1.8 kB was identified on the Northern blot from the RNA of the LPS-induced PMA-differentiated THP-1 cells. This indicated that a single 1.8-kb mRNA encoding the LITAF protein was present only in LPS-induced PMA-differentiated THP-1 cells. The size of the transcript was consistent with the sequence data. No band was detected from the RNA obtained from PMA-differentiated cells in the absence of LPS stimulation, nor in LPS-stimulated cells in the absence of PMA differentiation, nor in unstimulated THP-1 cells. Similar amounts of β-actin mRNA were detected by the Northern analysis of all samples.

Expression Patterns of LITAF in Human Tissue

Samples of different human tissues were assayed for LITAF expression by Northern blot hybridization analysis. The preblotted filters (Clonteck) containing the mRNA isolates were hybridized with an antisense RNA probe that corresponded to the coding region of the LITAF gene, as described in detail in the following Methods of the Invention section. This analysis identified a very strong band in RNA from spleen, lymph node and peripheral blood leukocytes, which migrated at approximately 1.8-kb, indicating that the 1.8-kb size transcript was significantly highly expressed in these tissues. Moderate expression was indicated in thymus, appendix, bone marrow, kidney and placenta, by the identification of a somewhat less pronounced band of the same size. Detectably lower expression was observed in pancreas, skeletal muscle, liver and lung, by an even less pronounced band. Expression was also detectable in heart, brain and fetal liver, although to a much lesser degree. The size of the detected transcripts was consistent with the sequence results and further suggests that the cDNA isolated was the full length clone.

The observed tissue expression of LITAF mRNA indicates that LITAF gene is expressed in most of the tissues tested, with predominance in hemato-lymphopoietic tissues and placenta, kidney and pancreas. Interestingly, this distribution of LITAF transcripts seems to parallel TNF-α tissue distribution during endotoxemia (Giroir et al., *B. J. of Clin. Invest.* 90: 693-8 (1992); Ruco et al., *American J. of Path.* 135: 889-97 (1989)).

Antisense and Sense LITAF mRNA Constructs and Expression

Recently, Neuenchwander et al. (Neuenchwander et al., *Endocrinology* 136: 4298-4303 (1995)) reported that stable antisense RNA expression inhibits the translation of sense RNA. In a number of documented studies (Stein, C. A., *Antisense and Nucleic Acid Drug Development* 8: 129-32 (1998); Helene et al., *Ciba Foundation Symposium* 209: 94-102 (1997); Morales and de Pablo, *Current Topics in Developmental Biology* 36: 37-49 (1998); Agrawal and Iyer, *Pharmacology & Therapeutics* 76: 151-60 (1997)), stable antisense RNA expression has resulted in a decrease in endogenous mRNA levels. Although the mechanism responsible for this decrease remains unclear, it is thought related to the inhibition of RNA synthesis, RNA splicing, mRNA export, binding of initiation factors, assembly of ribosome subunits and of sliding of the ribosome along the mRNA coding sequence, interference with any of which resulting in translation arrest (Kim and Wold, *Cell* 42: 129-138 (1985)). Motivated by these observations, experiments were designed to interfere with LITAF gene activity at the mRNA level by transfecting antisense oligonucleotide-producing vectors into THP-1 cells. The most common mRNA target site reported in the literature is the AUG translation initiation codon (Crooke and Lebleu, *Antisense Research and Therapeutic*, CRC Press, Boca Raton, Fla. (1993)). However, it has been found in many cases that oligonucleotides which target other regions in the mRNA, such as 5'- and 3'-untranslated regions are more effective (Bennett et al., *J. of Immun.* 152(7): 3530-40 (Apr. 1, 1994); Dean et al., *J. of Biol. Chem.* 269(23): 16416-24 (Jun. 10, 1994); Perlaky et al., *Anti-Cancer Drug Design* 8 (1): 3-14 (1993); Chiang et al., *J. of Biol. Chem.* 266(27): 18162-71 (1991)). Therefore to interfere with LITAF mRNA, a vector producing antisense oligonucleotides which target the 5' region of the LITAF mRNA was transfected, while for the overexpression of the LITAF mRNA a vector producing the full length of the LITAF mRNA was transfected.

THP-1 cells were transfected with the following expression constructs: LITAF antisense RNA (AS5'); LITAF sense RNA construct(SE), or vector alone. Stable transfection was verified by Northern blot analysis of RNA isolated from the recipient cells. Total RNA was recovered from cells after differentiation with PMA and stimulation with P.g. LPS. Using LITAF antisense RNA as a probe, a 1.8 kb transcript was detected in sense-transfected cells. A band of approximately 400 bp, corresponding to the size of the AS5' message, was detected in the antisense-transfected cells using the LITAF sense RNA as a probe. No band signal was detected in mock-transfected cells with either probe. Similar amounts of β-actin mRNA were found in LITAF antisense-expressing cells, LITAF sense-expressing cells and mock-transfected cells.

Effect of Antisense Expression of LITAF mRNA on Expression of TNF-α mRNA

Ribonuclease (RNase) protection assay was performed on the cells expressing the exogenous LITAF constructs, to determine the effects of expression of the LITAF sequences, sense and antisense, on TNF-α mRNA expression in the cells. Total RNA was recovered from cells after differentiation of the cells with PMA and stimulation with P.g. LPS. The obtained RNA was then hybridized with the TNF-α antisense RNA probe and treated with RNase A and T1. Protected bands were then identified. The intensity of the protected band in LITAF antisense-expressing cells compared to that in the mock-transfected cells was detectably weaker on a gel, indicating that the amount of TNF-α mRNA expressed was strongly reduced. There was no observable difference in the intensity of the protected band from the LITAF sense-expressing cells compared to the band from the mock-transfected cells, indicating a similar level of TNF-α mRNA expression. Similar amounts of β-actin mRNA were found in LITAF antisense-expressing cells, LITAF sense-expressing cells, and mock-transfected cells.

The reduction of TNF-α mRNA that occurs when LITAF gene mRNA activity was arrested indicates that the LITAF gene product plays an important role in the regulation of human TNF-α gene transcription. In addition, the expression level of TNF-α mRNA was not enhanced in the sense-expressing cells. Without being bound by theory, there are three possibilities for how the LITAF gene product may regulate gene transcription: (1) the LITAF gene may have to be processed as a protein to activate the TNF-α gene; (2) the endogenous LITAF gene product is enough to activate the TNF-α gene; and (3) the exogenous LITAF gene product acts after protein processing because a large amount of LITAF mRNA is constitutively transcribed in the cells. The present data supports other recent data suggesting that LPS induction of the TNF-α promoter is mediated by the concerted participation of at least two separate cis-acting regulatory elements (Yao et al., *J. of Biol. Chem.* 272(28): 17795-801 (1997)), and suggests that LITAF is a necessary participant.

Chromosome Localization of the LITAF Gene

To identify the location of the LITAF gene, FISH analysis was performed on a metaphase chromosome spread after hybridization with a biotinylated LITAF cDNA probe. Specific labeling was observed on chromosome 16. The location on Chromosome 16 α-satellite was confirmed by double labeling with a commercial probe D16Z2 (Oncor Inc.). The probe had specificity for this site, since symmetrical signals were not observed on other chromosomes. The FISH signals were localized relative to the chromosomes bands and the LITAF gene locus assigned to Chromosome 16 p12-16p13.3.

Discussion

The potential role of LITAF in human disease is implicated by the recent finding that p53 induces the expression of LITAF gene (Polyak et al., *Nature*, September 18;389(6648): 300-305 (1997)) and by its chromosomal localization at 16p12-16p13.3. The p53 tumor suppressor protein is thought to play a major role in the defense of the cell against agents which damage DNA (Carson and Lois, *Cancer Progression and p53. Lancet* 346(8981): 1009-11 (1995); Sherr, C. J., *Science* 274: 1672-7 (1996)). Loss of function of the p53 tumor suppressor gene is a frequent and important event in the genesis or progression of many human malignancies. Loss of p53 dependent apoptosis is believed to be critical to carcinogenesis in many of these cases, suggesting the possibility to therapeutically restore this pathway and directly eliminate malignant cells or increase or restore their sensitivity to chemotherapeutic agents (Carson and Lois, *Cancer Progression and p53. Lancet* 346(8981): 1009-11 (1995); Sherr, C. J., *Science* 274: 1672-7 (1996)). The regulation of p53-dependent responses is complex and variable between cell types, and whether a cell undergoes apoptosis after activation of p53 is highly sensitive to signal context, including environmental and cell intrinsic influences.

Further insight has been provided into the activation of latent p53, the biochemical mechanisms involved in growth arrest and apoptosis, and the influence of various signals on these cellular effects. Additionally, roles for p53 have been described in cell senescence, in suppressing teratogenesis, and in processes that may directly contribute to the maintenance of genomic stability (Carson and Lois, *Cancer Progression and p53. Lancet* 346(8981): 1009-11 (1995); Sherr, C. J., *Science* 274: 1672-7 (1996)).

Recently, various monocytic cell lines have been shown to respond to LPS and INF-γ with endogenous nitric oxide formation (Brune et al., *J. of Biol. Chem.* 272: 7253-8 (1997)) which in turn activate the expression of p53 leading to apoptosis (Shapira et al., *Infect. Immun.* 66: 2736-42 (1998)). Furthermore, p53 has been recently shown to modulate the activity of various inflammatory cytokines such as IL-6 (Margulies and Sehgal, *J. Biol. Chem.* 268: 15096-100 (1993)), IL-2 and IL-4 (Pesch et al., *J. Interferon Cytokine Res.* 16: 595-600 (1996)).

In light of the present data, a potential new p53-dependent pathway affecting TNF-α gene expression can be proposed: LPS stimulation of monocyte/macrophages can induce NO production. In turn NO can upregulate p53 which would stimulate expression of the LITAF gene. Ultimately, the induction of the LITAF gene product would affect TNF-α gene expression. Altogether, the present data suggest that the novel LITAF gene product is a crucial factor for the control of TNF-α gene expression.

Methods of the Invention

Cell Culture. The human monocytic cell line, THP-1, was maintained in complete RPMI (C-RPMI) (RPMI 1640 medium supplemented with 2 mM L-glutamine, 25 mM HEPES [N-2-hydroxyethypiperazine-N'-2-ethanesulfonic acid], 100 units/ml of penicillin, 100 mg/ml of streptomycin, and 10% fetal bovine serum [all from GIBCO, Gaithersburg, Md.]). LPS-free tissue culture reagents were used for all experiments.

Preparation of Nuclear Extracts from Cultured THP-1 Cells. THP-1 cells were induced to maturation by incubation in 200 nM PMA (Sigma, St. Louis, Mo.) for 20 hrs and then stimulated with 100 ng/ml of *Porphyromonas gingivalis* (P.g) LPS (Shapira et al., *Oral Microbiol. Immunol.* 9: 112-117 (1994)) for 2 hrs. Nuclear extracts were prepared as described previously (Takashiba et al., *Infect. Immun.* 63: 1529-1534 (1995)).

Preparation of DNA Affinity Beads. The 64-bp initiator element located from -550 to -487 in the human TNF-α promoter (Takashiba et al., *Gene* 131: 307-308 (1994)) was amplified by PCR. The PCR mixture (50 ml) was prepared as described previously (Takashiba et al., *Gene* 131: 307-308 (1994)). The human TNF-α promoter (Takashiba et al., *Gene* 131: 307-308 (1994)) was used as the template for the PCR. The sequence 5'-TGAGGCCTCAAGCTGCCACCA-3' (SEQ ID NO: 4) was used for the forward primer sequence and 5'-TGAGGCCTGTGTTTGGGTCTG-3' (SEQ ID NO: 5) for the reverse sequence, with biotin attached to the 5' end. The cycling parameters (30 cycles) were as follows: an initial denaturation at 94° C. for 1 min, annealing at 55° C. for 1 min, and elongation at 72° C. for 1 min. The last cycle had an additional elongation time of 7 min. The PCR products were separated on an agarose gel, and the 64-bp DNA band was cut from the gel. The unincorporated biotinylated primers were removed using the QIAEX II Gel Extraction Kit (Qiagen Inc., Santa Clarita, Calif.). The biotinylated DNA was desalted and dissolved in Tris-HCl EDTA (2 mg/ml) and then used for the preparation of DNA affinity beads. Immobilization of labeled DNA to Dynabeads M-280 streptavidin (10 mg/ml; Dynal, Inc., Lake Success, N.Y.) was performed as described by Gabrielsen et al. (Gabrielsen and Huet, *Methods in Enzymology* 218: 508-525 (1993)). Briefly, a suspension of beads was coupled with the labeled DNA at room temperature for 30 min. The affinity beads were washed to remove unbound DNA and then used for purification of DNA-binding protein.

Purification of DNA-Binding Protein Using Affinity Beads. Purification of the protein which binds to the affinity beads was performed as described previously (Gabrielsen and Huet, *Methods in Enzymology* 218: 508-525 (1993)). Briefly, the nuclear extracts were incubated with the beads in binding buffer containing poly (dI-dC) at room temperature. After washing (twice), the DNA-binding protein was eluted, desalted, and then used for further analysis.

Isolation of the DNA-Binding Protein and Sequence Analysis. The eluted protein sample was separated by 12% SDS-polyacrylamide gel electrophoresis (SDS-PAGE) as described previously (Takashiba et al., *Infect. Immun.* 63: 1529-1534 (1995)). The resolved proteins (approximately 2% of the protein of the total protein) were electroblotted onto a polyvinylidene difluoride membrane as described by Matsudaira (Matsudaira, P., *J. Biol. Chem.* 262: 10035-10038 (1987)) and stained with Coomassie blue. A predominant stained protein band with an apparent molecular weight of 60 kd was excised. After treatment with trypsin (Fernandez et al., *Anal. Biochem.* 201: 255-264 (1992)), the resultant peptides were separated by high-performance liquid chromatography on a C18 column with a 0 to 100% acetonitrile gradient containing 0.01% trifluoroacetic acid (Fernandez et al., *Anal. Biochem.* 201: 255-264 (1992)). Fractions were collected, and a number of peptides were sequenced by established methods as previously described (Matsudaira, P., *J. Biol.*

Chem. 262: 10035-10038 (1987)). All peptide sequences determined were later correlated with the isolated cDNA clone. Degenerate oligonucleotides (16 mer) corresponding to either end of peptide #1 M-S-V-P-G-P-Y-Q-A-A-T-G (SEQ ID NO: 3) were used for PCR, using the LPS-induced THP-1 cDNA as a template to obtain a DNA fragment containing the exact nucleotide sequences encoding the middle part of this peptide. PCR products resolved in an 8% acrylamide gel were eluted using the QIAEX II Gel Extraction Kit (Qiagen) and subcloned into a PCRII vector (Invitrogen, San Diego, Calif.). Sequencing verified the fidelity of the PCR products.

Screening the cDNA Library. An LPS-stimulated, PMA-induced, custom-made human THP-1 Uni-ZAP™ XR cDNA library (Stratagene, La Jolla, Calif.) was screened using this PCR probe, and nine positive clones containing 0.8- to 1.8-kb inserts were obtained after screening $5 \times 10^5$ colonies. The longest cDNA insert (1.8 kb) was chosen for complete sequencing by dideoxynucleotide chain-termination method using a 373A sequencer (ABI).

The BLAST program was used to search the database through the NCBI. The PILEUP and PRETTYBOX programs were used for sequence alignments and comparisons. The FASTA program was used for calculating the protein identities. All these computer programs were from the Wisconsin Genetics Computer Group, Madison, Wis. Finally the SIGSCAN program was used to search the Transcription Factor Database (TFD) through the BIMAS program of the Advanced Biosciences Computing Systems maintained at the University of Minnesota.

Figure 1A:
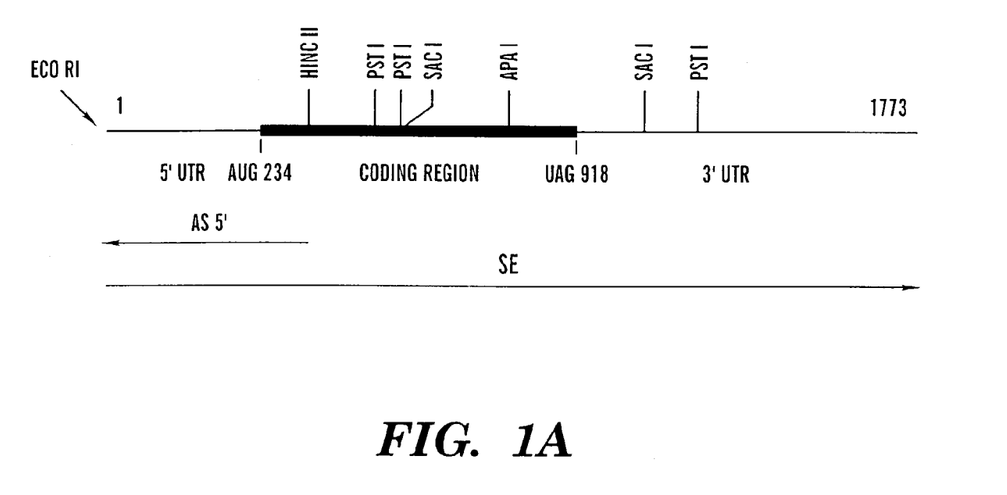
Figure 1B:
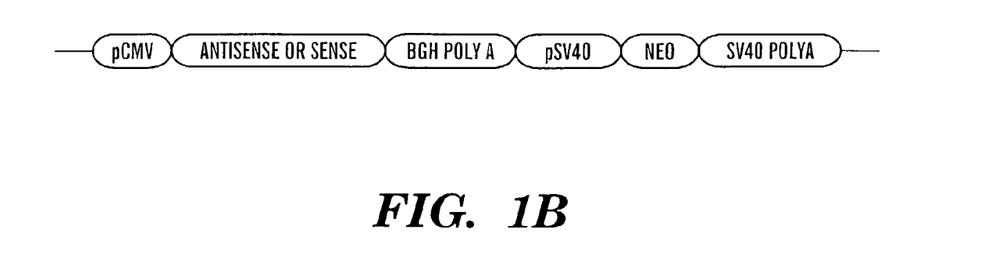
FIG. 1B is a schematic structure of the antisense or sense constructs inserted downstream to the CMV promoter.

Generation of Probes. The 511 bp of the Hinc II-Apa I cDNA fragment from the coding sequence in the new gene (FIGS. 1A and B) was subcloned into pGEM7Zf(+) (Promega). The antisense and sense riboprobes were prepared from this plasmid and labeled with $^{35}$S-UTP as previously described (Ausubel et al., (1992) In *Short Protocols in Molecular Biology*, 3rd Ed., New York, Greene Publishing and Wiley-Interscience). These probes were used for Northern blot hybridizations.

Detection of LITAF Gene Transcripts. THP-1 cells ($5 \times 10^6$) were induced to maturation by incubation in 200 nM PMA (Sigma) for 20 hrs and then stimulated with 100 ng/ml of P.g. LPS (Shapira et al., *Oral Microbiol. Immunol.* 9: 112-117 (1994)) for 2 hrs. THP-1 cells induced to maturation without stimulation by p.g. LPS were also used. Noninduced THP-1 cells were also cultured, with and without stimulation with p.g. LPS. Total cellular RNA was collected from cells having undergone each of these culture conditions using RNA STAT-60 (TEL-TEST"B" Inc., Friendswood, Tex.) by the method described in the instruction manual, and polyadenylated [poly (A)$^+$] RNA (mRNA) was recovered using the Oligotex mRNA Kit (Qiagen). mRNA was size-fractionated on denaturing formaldehyde-agarose gel (1.1%) and transferred onto a Hybond-N$^+$ membrane (Amersham Corp., Arlington Heights, Ill.) as previously described (Ausubel et al., (1992) In *Short Protocols in Molecular Biology*, 3rd Ed., New York, Greene Publishing and Wiley-Interscience).

Northern blot filters with mRNA from several different human tissues (adult unless otherwise indicated) were obtained from Clontech. The tissues were heart, brain, placenta, lung, liver skeletal muscle, kidney, pancreas, spleen, lymph node, thymus, appendix, peripheral blood leukocyte, bone marrow, and fetal liver. These filters were hybridized with a $^{35}$S-labeled cRNA probe at 60° C. overnight in 50% formamide, 5×SSC, 5× Denhardt's solution, 0.1% SDS, 50 mm sodium phosphate (pH 6.9), and heat-denatured salmon sperm DNA. The filters were washed three times in 0.1×SSC, 0.1% SDS at 68° C. for 30 min, and then autoradiographed with BIOMAX™ MR film (Kodak, Rochester, N.Y.).

Antisense and Sense Construct. Eukaryotic expression vectors (pRc/CMV; Invitrogen) were constructed as described previously (Maret et al., *Cancer Res.* 55: 5075-5079 (1995); Boshart et al., *Cell* 41: 521-530 (1985)) with slight modifications. Briefly, the LITAF cDNA fragments (indicated below and in FIGS. 1A and B) were placed in either an antisense orientation or a sense orientation downstream of the human cytomegalovirus (CMV) promoter element as the first open reading frame. The vector contained a neo-resistance gene for selection of stable transfectants. Plasmid constructions were as follows: AS5', antisense cDNA corresponding to a 320-bp fragment that covered the 5' UTR and the AUG start codon; SE, sense full length of cDNA; and CON, control vector without insert. These constructions are illustrated in FIG. 1. All plasmids were prepared using Qiagen Plasmid Midiprep Kits (Qiagen).

Stable Transfection. THP-1 cells ($5 \times 10^6$/cuvette) were transfected by electroporation (Gene Pulser™, BIO RAD, Hercules, Calif.) with 20 mg of recombinant plasmid according to the manufacturer's instructions. Mock cells were similarly transfected with a control vector (pRcCON). Two days later, cells were cultured in C-RPMI containing 0.8 mg/ml of G418 (Geneticin; GIBCO). This medium was changed every 3 days. The surviving cells were used for further experimentation.

Monitoring of Exogenous mRNA Expression. Success of stable transformation was confirmed by Northern blot analysis with antisense and sense riboprobes. Total cellular RNA was recovered from transfected cells ($2 \times 10^6$) and used for Northern blot analysis in a manner similar to that previously described. The 707 bp of the Eco RI-Sac I cDNA fragment, which contained 5' UTR and a coding sequence for the new gene (FIG. 1A and B), was subcloned into pbluescript SKII (−). The $^{35}$S-labeled riboprobes for hybridization were prepared from this plasmid as described previously (Ausubel et al., (1992) In *Short Protocols in Molecular Biology*, 3rd Ed., New York, Greene Publishing and Wiley-Interscience).

Quantitation of TNF-α mRNA Expression in Transfected Cells. TNF-α mRNA expression was quantitated using a ribonuclease (RNase) protection assay. Transformed THP-1 cells ($2 \times 10^6$) were incubated with 200 nM of PMA (Sigma) for 20 hrs to induce differentiation and then stimulated with 100 ng/ml of P.g. LPS (Shapira et al., *Oral Microbiol. Immunol.* 9: 112-117 (1994)) for 2 hrs. mRNA was recovered from the cells as previously described. Successful recovery of mRNA from each sample was monitored by Northern blot hybridization with a β-actin probe. The 355-bp TNF-α cDNA was obtained from a PMA-induced human THP-1 Uni-ZAP™XR cDNA library (Stratagene) by PCR with specific primers for TNF-α mRNA (Stratagene). After the cDNA was subcloned to a SmaI site of pGEM7Zf(+), the TNF-α cDNA was identified by sequencing. After the plasmid was linearized with XbaI and transcribed with SP6 polymerase, a 446-bp $^{35}$S-labeled antisense probe was constructed. The RNase protection assays were performed as previously described (Ausubel et al., (1992) In *Short Protocols in Molecular Biology*, 3rd Ed., New York, Greene Publishing and Wiley-Interscience).

Fluorescence In Situ Hybridization. The LITAF full length cDNA probe was nick translated with biotin using kit No. S4099 (Oncor, Gaithersburg, Md.) according to manufacturer's instructions. One-half microgram of human Cot-1 DNA and 75 μg of salmon sperm DNA were resuspended in 50 μl of hybrisol VII (Oncor, Cat. No. S1390-10) by sonication. The probe was denatured at 70° C. for 5 min and incubated at 37°

C. for 30 min for biotin labeling prior to mixing with the D16Z1 probe. A digoxygenin-labeled D16Z1 Chromosome 16 α-satellite Probe (Oncor, Cat. No. P5035-DG-5) was denatured at 70° C. for 5 min and used to confirm the location of the LITAF gene on chromosome 16. Normal lymphocytes were treated with colcemid to arrest cell division, harvested, fixed, and placed onto slides according to standard cytogenetic protocols. The slides were denatured in 2×SSC (pH 7.0) plus 70% formamide at 72° C. for 2 minutes, followed by dehydration in a series of ethanol rinses. Equal volummes of labeled, denatured probes were mixed, and 20 μl was added to each dehydrated slide. Hybridization proceeded for 15 to 17 hours at 37° C. The slides were washed for 15 min at 43° C. in 2×SSC plus 65% formamide and then at 37° C. for 8 minutes in 2×SSC. The biotin-labeled probe was detected by binding to avidin-Texas red, washed, amplified with anti-avidin, washed, and amplified with avidin-Texas red using the Biotin-Texas Red Detection Kit (Oncor, Cat. No. S1334-BTR) according to manufacturer's instructions. The digoxygenin-labeled hybridized probe was detected with FITC-labeled anti-digoxygenin antibody, washed, amplified with rabbit-anti-sheep antibody, washed, and amplified with FITC-anti-rabbit antibody (Digoxygenin-FITC Detection Kit, Cat. No. S1331-DF) according to manufacturer's instructions. The slides were counterstained with DAPI and photographed using triple-excitation/emission bandpass filters (Olympus, Tokyo, Japan, Cat. No 61002X).

Generation of antibodies specific for LITAF. The CGC program was to determine the Jameson Wolf antigenic index of the amino acid sequence of the LITAF protein. This index predicts the regions of the polypeptide expected to be the most immunogenic when introduced into an animal for the elicitation of an immune response. Three regions, corresponding to 1) amino acids 25-40, 2) amino acids 60-80, and 3) amino acids 180-195 of the LITAF protein, were identified as likely immunogenic areas of the LITAF protein Three synthetic polypeptides were generated which had amino acid sequences directly corresponding to these regions, and used to generate polyclonal antibodies. The synthetic polypeptides were linked to the carrier protein keyhole limpet hemocyanin (KLH), by standard techniques, and used to generate rabbit polyclonal antibodies (Methods in Molecular Biology, Volume 51: p 165-170 (1995) Antibody Engineering protocols. Editor Fudhir Paul, publisher Humana Press, Totowa, N.J.). Separate rabbits were immunized with the different polypeptide antigens. Complete Freunds adjuvant was used in the initial inoculations, and incomplete Freunds adjuvant was used in subsequent boost inoculations.

ELISA analysis was used to identify and quantitate the presence of antibodies specific for the polypeptides in the serum obtained from the rabbits. The respective polypeptides were used in the ELISA. The antigen which contained the polypeptide sequence corresponding to amino acid 180-195 of LITAF produced the highest titer of antibody, with dilutions of up to 1:32,000 demonstrating activity via ELISA analysis. Immunization with the antigen which contained the polypeptide sequence corresponding to amino acids 60-80 of LITAF also produced a significant titer. The antigen which contained the polypeptide sequence corresponding to amino acid 25-40 of LITAF produced the weakest response. The antisera which was raised to each of the polypeptides was able to identify full length recombinant LITAF via Western blot analysis.

Antibody generated to the antigenic polypeptide comprised of amino acids 180-195 of LITAF was then affinity purified from the sera using the synthetic polypeptide by the methods described in (Methods in Molecular Biology, Volume 51: p 165-170 (1995) Antibody Engineering protocols. Editor Fudhir Paul, publisher Humana Press, Totowa, N.J.).

This affinity purified antibody was then used in immunogold immunocytochemistry, probing human monocyte macrophages (Nanci, A. et al., *Journal of Histochemistry & Cytochemistry* 33: 1153-1160 (1985)). Probing resulted in high specific staining in the nucleus, particularly the chromatin, which is where the LITAF protein is expected to be found in the cell. These results indicate that the above described antibodies specifically recognize and bind to native LITAF and recombinant LITAF.

The invention claimed is:

1. A method for inhibiting lipopolysaccharide-induced tumor necrosis factor-alpha factor (LITAF)-dependent induction of tumor necrosis factor-alpha (TNF-α) gene expression in a human cell comprising the steps:
   a) providing an antisense oligonucleotide that reduces or inhibits expression of the LITAF gene, wherein said antisense oligonucleotide comprises a sequence that is complementary to at least 150 contiguous nucleotides set forth within nucleotides 1-320 of SEQ ID NO: 2 including the start site of translation beginning at nucleotide 234 of SEQ ID NO: 2; and
   b) delivering the antisense oligonucleotide into said cell; wherein said antisense oligonucleotide reduces or inhibits LITAF-dependent TNF-α gene expression in said cell.

2. The method of claim 1, wherein said antisense oligonucleotide comprises a sequence that is complementary to at least 200 contiguous nucleotides.

3. The method of claim 1, wherein the antisense oligonucleotide further comprises a sequence that is complementary to the downstream adjacent 3' coding sequence set forth in SEQ ID NO: 2.

4. The method of claim 1, wherein said antisense oligonucleotide comprises a sequence that is complementary to at least 320 contiguous.

5. The method of claim 4, wherein the antisense oligonucleotide comprises a sequence that is complementary to nucleotides 1-320 of SEQ ID NO: 2.

6. The method of claim 1, wherein said antisense oligonucleotide is encoded within a viral vector.

7. The method of claim 6, wherein said viral vector is an adenoviral vector.

8. The method of claim 1, wherein said antisense oligonucleotide is formulated in a liposome carrier.

9. The method of claim 1, wherein said antisense oligonucleotide is a ribonucleic acid (RNA) molecule.

* * * * *

UNITED STATES PATENT AND TRADEMARK OFFICE
CERTIFICATE OF CORRECTION

PATENT NO. : 7,626,007 B2
APPLICATION NO. : 10/405738
DATED : December 1, 2009
INVENTOR(S) : Salomon Amar It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 503 days.

Signed and Sealed this

Second Day of November, 2010

David J. Kappos
*Director of the United States Patent and Trademark Office*

SEQUENCE LISTING

```
<160> NUMBER OF SEQ ID NOS: 5

<210> SEQ ID NO 1
<211> LENGTH: 228
<212> TYPE: PRT
<213> ORGANISM: Homo sapiens

<400> SEQUENCE: 1

Met Ser Val Pro Gly Pro Tyr Gln Ala Ala Thr Gly Pro Ser Ser Ala
  1               5                  10                  15

Pro Ser Ala Pro Pro Ser Tyr Glu Glu Thr Val Ala Val Asn Ser Tyr
                 20                  25                  30

Tyr Pro Thr Pro Pro Ala Pro Met Pro Gly Pro Thr Thr Gly Leu Val
             35                  40                  45

Thr Gly Pro Asp Gly Lys Gly Met Asn Pro Pro Ser Tyr Tyr Thr Gln
         50                  55                  60

Pro Ala Pro Ile Pro Asn Asn Asn Pro Ile Thr Val Gln Thr Val Tyr
 65                  70                  75                  80

Val Gln His Pro Ile Thr Phe Leu Asp Arg Pro Ile Gln Met Cys Cys
                 85                  90                  95
```

Pro Ser Cys Asn Lys Met Ile Val Ser Gln Leu Ser Tyr Asn Ala Gly
            100                 105                 110

Ala Leu Thr Trp Leu Ser Cys Gly Ser Leu Cys Leu Leu Gly Val His
            115                 120                 125

Ser Gly Leu Leu Leu His Pro Leu Leu Arg Gly Cys Pro Ala Gly Arg
            130                 135                 140

Gly Pro Leu Leu Ser Gln Leu Gln Ser Ser Pro Gly His Leu Gln Ala
145                 150                 155                 160

Phe Val Gly Leu Ser Gln Thr Gln Arg Glu Pro Gly Ala Ala Gly Ser
                165                 170                 175

Pro Phe His Leu Ser Ser Ser Phe Thr Pro Gly Gly Ser Ala Leu
            180                 185                 190

Val Val Ser Pro Leu Gln Gly Ala His Leu His Val Phe Phe Trp Gly
            195                 200                 205

Glu Tyr Val Ala Lys Leu Thr Asn Leu Gln Thr Pro Glu Ile Ala Ala
    210                 215                 220

Trp Ser Arg Ala
225

<210> SEQ ID NO 2
<211> LENGTH: 1773
<212> TYPE: DNA
<213> ORGANISM: Homo sapiens

<400> SEQUENCE: 2

| | | | | | |
|---|---|---|---|---|---|
| gtttctctcc | ctgccccgc | gacttcgcgc | aagatccggg | aaggacaccc | gaggcccctg | 60 |
| ggagaccctg | ggaggtgaa | agtcagagag | cgaagcgggc | cgtggcccct | aggcctgacc | 120 |
| cctccccgcg | gggtaaggcg | ggcaccccgc | gagcgcaggg | gtcctcttac | tgctgatggc | 180 |
| acccagctct | gggcccagac | gccgctcacc | gtccaccgcc | ggtgctgggt | aaaatgtcgg | 240 |
| ttccaggacc | ttaccaggcg | gccactgggc | cttcctcagc | accatccgca | cctccatcct | 300 |
| atgaagagac | agtggctgtt | aacagttatt | accccacacc | tccagctccc | atgcctgggc | 360 |
| caactacggg | gcttgtgacg | gggcctgatg | ggaagggcat | gaatcctcct | tcgtattata | 420 |
| cccagccagc | gcccatcccc | aataacaatc | caattaccgt | gcagacggtc | tacgtgcagc | 480 |
| accccatcac | cttttggac | cgccctatcc | aaatgtgttg | tccttcctgc | aacaagatga | 540 |
| tcgtgagtca | gctgtcctat | aacgccggtg | ctctgacctg | gctgtcctgc | gggagcctgt | 600 |
| gcctgctggg | ggtgcatagc | gggctgctgc | ttcatcccct | tctgcgtgga | tgccctgcag | 660 |
| gacgtggacc | attactgtcc | caactgcaga | gctctcctgg | gcacctacaa | gcgtttgtag | 720 |
| gactcagcca | gacgtggagg | gagccgggtg | ccgcaggaag | tcctttccac | ctctcatcca | 780 |
| gcttcacgcc | tggtggaggt | tctgccctgg | tggtctcacc | tctccagggg | gccaccttc | 840 |
| atgtcttctt | tgggggaa | tacgtcgcaa | aactaacaaa | tctccaaacc | ccagaaattg | 900 |
| ctgcttggag | tcgtgcatag | gacttgcaaa | gacattcccc | ttgagtgtca | gttccacggt | 960 |
| ttcctgcctc | cctgagaccc | tgagtcctgc | catctaactg | tgatcattgc | cctatccgaa | 1020 |
| tatcttcctg | tgatctgcca | tcagtggctc | ttttttcctg | cttccatggg | cctttctggt | 1080 |
| ggcagtctca | aactgagaag | ccacagttgc | cttattttg | aggctgttct | gcccagagct | 1140 |
| cggctgaacc | agcctttagt | gcctaccatt | atcttatccg | tctcttcccg | tccctgatga | 1200 |
| caaagatctt | gccttacaga | ctttacaggc | ttggctttga | gattctgtaa | ctgcagactt | 1260 |
| cattagcaca | cagattcact | ttaatttctt | aatttttttt | ttaaatacaa | ggaggggct | 1320 |

```
attaacaccc agtacagaca tatccacaag gtcgtaaatg catgctagaa aaatagggct    1380
ggatcttatc actgccctgt ctccccttgt ttctctgtgc cagatcttca gtgccccttt    1440
ccatacaggg attttttct catagagtaa ttatatgaac agtttttatg acctccttt     1500 ggtctgaaat acttttgaac agaatttctt tttttaaaa aaaaacagag atggggtctt    1560
actatgttgc ccaggctggt gtcgaactcc tgggctcaag cgatccttct gccttggcct   1620
cccgaagtgc tgggattgca ggcataagct accatgctgg gcctgaacat aatttcaaga   1680
ggaggattta taaaaccatt ttctgtaatc aaatgattgg tgtcattttc ccatttgcca   1740
atgtagtctc acttaaaaaa aaaaaaaaaa aaa                                1773

<210> SEQ ID NO 3
<211> LENGTH: 12
<212> TYPE: PRT
<213> ORGANISM: Homo sapiens

<400> SEQUENCE: 3

Met Ser Val Pro Gly Pro Tyr Gln Ala Ala Thr Gly
  1               5                  10

<210> SEQ ID NO 4
<211> LENGTH: 21
<212> TYPE: DNA
<213> ORGANISM: Homo sapiens

<400> SEQUENCE: 4
tgaggcctca agctgccacc a                                               21

<210> SEQ ID NO 5
<211> LENGTH: 21
<212> TYPE: DNA
<213> ORGANISM: Homo sapiens

<400> SEQUENCE: 5
tgaggcctgt gtttgggtct g                                               21
```